United States Patent [19]

Byerley

[11] Patent Number: 5,672,833

[45] Date of Patent: Sep. 30, 1997

[54] PEAK FLOW METER FOR MEASURING VENTILATORY CAPACITY

[75] Inventor: Stephen William Byerley, Harlow, England

[73] Assignee: Clement Clark International, Ltd., Harlow, England

[21] Appl. No.: 593,911

[22] Filed: Jan. 30, 1996

[30] Foreign Application Priority Data

Feb. 16, 1995 [GB] United Kingdom ............... 9502996

[51] Int. Cl.⁶ ........................................... A61B 5/087
[52] U.S. Cl. ..................... 73/861.55; 128/725; 73/861.53
[58] Field of Search .................... 73/861.76, 861.75, 73/861.55, 861.53, 861.57, 239; 128/725, 726, 716, 719, 730

[56] References Cited

U.S. PATENT DOCUMENTS 4,041,935  8/1977  Garbe ......................... 73/239
5,003,828  4/1991  Van Den Burg ............... 128/726
5,224,487  7/1993  Bellofatt et al. .............. 128/725
5,357,972  10/1994  Norlien ....................... 128/725

FOREIGN PATENT DOCUMENTS 2064324  6/1981  United Kingdom.

*Primary Examiner*—Richard Chilcot
*Assistant Examiner*—Harshad Patel
*Attorney, Agent, or Firm*—Jones, Tullar & Cooper, P.C.

[57] ABSTRACT

A peak flow meter has a body forming a chamber along which a piston can be moved against the force of a spring by a subject exhaling through an inlet into the chamber. A slot runs along a side of the chamber to allow the air to escape and a pointer is movable along the slot by the piston to indicate its maximum displacement. A deflector at the chamber inlet concentrates the flow through the chamber towards the side at which the slot is located. By the use of such a deflector it is possible to measure reliably relatively small peak exhalation rates.

13 Claims, 1 Drawing Sheet

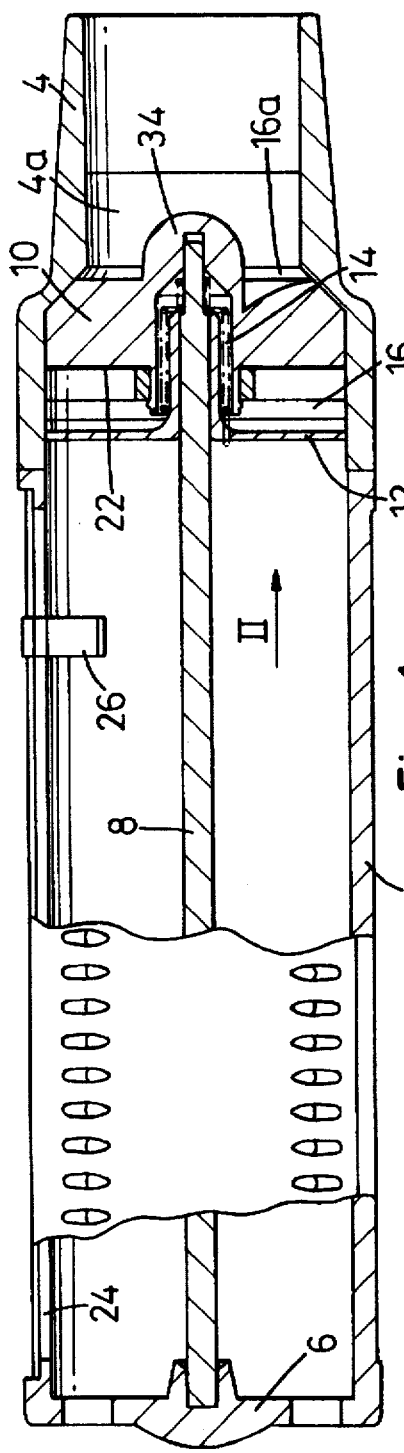
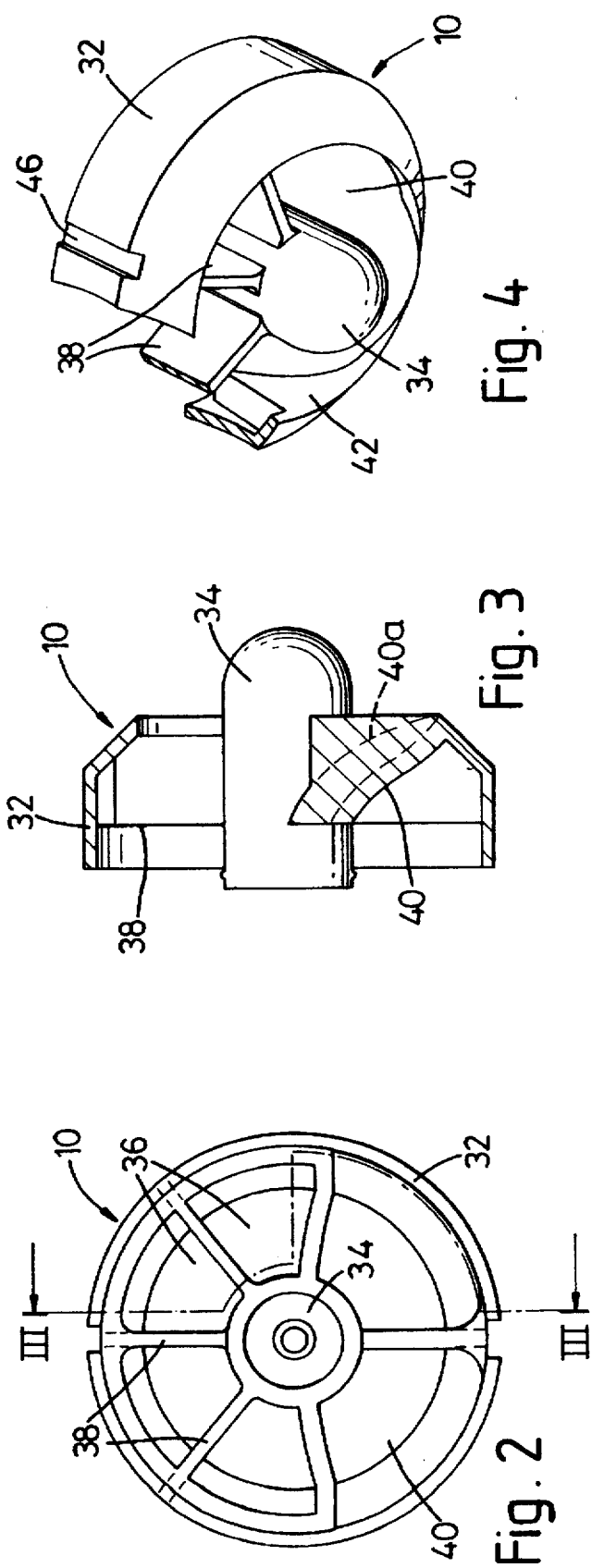

2

PEAK FLOW METER FOR MEASURING VENTILATORY CAPACITY

BACKGROUND OF THE INVENTION

This invention relates to meters for measuring the ventilatory capacity of a subject, in particular the exhalation capabilities of a subject.

Meters for obtaining a measure of the peak flow rate of exhalation are known in which the subject blows into one end of a chamber to displace a piston along the tube against the force of a spring. The chamber has an open slot running in the direction of piston displacement which provides an exit opening for the air being blown in. The piston is therefore drawn back by the spring when the intensity of exhalation falls. An indicating member located behind the piston has a light frictional engagement with the slot and is displaced by the piston as it moves forward against the spring force. When the piston moves back, the member remains at the position of maximum displacement of the piston, so giving an indication of the maximum flow rate obtained in the exhalation.

Such instruments will be referred to herein as "meters of the kind described". One example appears in GB 1463814.

Existing meters of the kind described can provide a satisfactory and consistent measure of the normal subject's breath but have found to be less suitable for measuring low flow rates, as in the case of a subject with asthmatic symptoms. The low scale values obtained on a meter designed for normal subjects are more difficult to read, which is particularly relevant because meters of the kind described are often required to be used by patients in their own homes. The fact that readings can be obtained only in the lower part of the scale of the instrument is also a significant disadvantage from the point of view of the self-confidence of the patent.

The metering range can be altered by changing the spring strength and the dimensions of the instrument to allow for a smaller airflow rate, but it is found that if this is done to such an extent as to provide an instrument with a maximum scale reading substantially less than that required for normal subjects, e.g. 400 l/min instead of 800 l/min, it is no longer possible to obtain consistent peak flow measurements: the results will be unduly affected by differences in the time profile of an exhalation.

It has now been discovered that there is a way in which this problem can be mitigated or avoided.

SUMMARY OF THE INVENTION

According to the present invention, there is provided a meter for measuring the ventilatory capacity of a subject comprising a chamber, a piston within the chamber being displaceable against a resilient bias by blowing into an inlet air passage to the chamber, an exit slot located in a side of the chamber for the escape of air from the chamber being increasingly opened by said displacement of the piston against its bias, and indicator means for indicating the maximum said displacement of the piston by the incoming air, said air passage at the chamber inlet being formed with deflection means which concentrates the air flow towards that side of the chamber at which the exit slot is situated.

Typically the chamber is provided with a tubular mouthpiece through which the subject blows air into the chamber. In such an arrangement the deflection means preferably take the form of a boundary wall that is inclined with respect to the longitudinal axis of the mouthpiece so that in the direction of the air flow it slopes towards the slot.

By way of example, an embodiment of the invention will be described with reference to the accompanying drawings.

BRIEF DESCRIPTION OF THE DRAWINGS

FIG. 1 is an axial sectional view of a peak flow meter for measuring the exhalation of a subject, FIG. 2 is an end view of the retainer member in the mouthpiece of the meter of FIG. 1, from the direction II in FIG. 1, FIG. 3 is a sectional view of the retainer member on the section line III—III in FIG. 2, and FIG. 4 is a partly broken-away isometric view of the retainer member.

DESCRIPTION OF THE PREFERRED EMBODIMENT

The instrument shown comprises a hollow cylindrical body 2 having a mouthpiece 4 at one end and an apertured closure member 6 at its opposite end. A support rod 8 extends through the interior of the body and is attached at one end to the closure member 6 and at the other to a retainer member 10 fixed in the mouthpiece 4. A piston 12 dividing the interior of the body is freely slidable on the rod. The piston 12 is attached by a coil spring 14 to the end of the rod 8 within the retainer member 10, and is drawn by the spring to the rest position shown, at the inlet end of the body 2, where it defines with the retainer member an internal chamber 16.

The retainer member 10 at the chamber inlet 16a has openings that are closed by a thin diaphragm 22 of readily flexible material acting as a non-return valve.

When the subject blows into the mouthpiece, the diaphragm 22 is flexed away and air flows through inlet passage 4a into the chamber formed between the retainer member 10 and the piston 12 as the air pressure drives the piston away from the retainer. As the piston moves along the support rod 8, it uncovers a longitudinal slot 24 in the container wall through which the flow can escape. A pointer 26 is mounted in the slot and has a light frictional engagement with its edges. The displacement of the piston away from the retainer member entrains the pointer along the slot but the pointer is not attached to the piston. Thus, when the pressure in the chamber 16 falls as the rate of exhalation through the mouthpiece decreases, the spring 14 draws the piston back but the pointer 26 is retained frictionally at the position of maximum piston displacement. A scale (not shown) along the slot 24 then allows the peak exhalatory flow to be read off.

The features described so far are similar to those of known meters of the kind described which may be arranged to record peak flows up to some 800 l/min. The illustrated meter is however intended to be able to record satisfactorily a range of peak flows up to about half that rate. As has already been explained, however, merely scaling down the dimensions of the known meter and the force of its spring does not in itself produce a reliable instrument for such low-range measurements.

The illustrated instrument utilises a novel configuration at the entry to the chamber 16 to allow more consistent low-range measurements to be achieved. In this example, the retainer member 10 is formed with a rim 32 by which it is secured to the mouthpiece and a central boss 34 securing the rod 8, the annular region between rim and boss having a series of through-flow apertures 36 separated by radial ribs 38. The apertures 36 occupy approximately the upper half of the annular region and the remainder of that region is closed by an integral web 40 which forms a barrier sloping upwards towards the chamber 16. The radially outer edge of the web is bounded by a cylindrical wall 42 and the face of the web towards the mouthpiece inlet is convex in axial cross-section, as indicated at 40a in FIG. 3.

The retainer member also has a keyway 46 which fits a rib (not shown) in the mating surface of the mouthpiece to locate it angularly thereto. The mouthpiece rib may also engage a keyway (not shown) in the body 2 to locate it angularly relative to the body. In this way it is ensured that the retainer member is assembled with web 40 in a diametrically opposite position to that of the slot 24 in the body.

It is found, surprisingly, that with the presence of the flow-deflecting means at the entry to the chamber 16, a satisfactory smaller scale version of the known instrument can be provided for a substantially lower operating range than that of the known instrument. Measurement of peak flows in a range up to about half that available in the larger instrument can be made, without there being any sacrifice of stability of performance, i.e. for a range of different flow patterns, a similar response is obtained if the flow peak values are similar. It is also possible to arrange that the instrument has a substantially linear reading scale.

The precise reasons why such performance can be obtained by the means described, in contrast to unsatisfactory characteristics resulting from simply reducing the dimensions of the known instrument, are not clear. It is believed that the inclined barrier provided by the web 40, by deflecting the airflow towards the slot, reduces the degree of turbulence acting on the piston. The presence of the substantially planar ribs 38 at the through-flow apertures may also make a contribution by acting as flow-smoothing vanes.

It will be understood that although the illustrated example has been related to a known form of meter of the kind described, the invention is capable of wider application to other forms of ventilatory capacity meters to improve their performance.

I claim:

1. A meter for measuring the ventilatory capacity of a subject, comprising a hollow body, the hollow of said body providing a chamber, an air inlet passage to the chamber, a piston having an end position within the chamber adjacent said air inlet passage, resilient biasing means urging the piston towards said end position in the chamber, the piston being displaceable from said end position by the subject blowing through the inlet air passage into the chamber, a boundary wall of said hollow body defining said chamber extending away from said inner inlet passage, an air exit slot extending along said boundary wall of the chamber away from said air inlet passage for the escape of air from the chamber, said exit slot being increasingly opened by said displacement of the piston from its end position, indicator means for indicating the maximum said displacement of the piston, deflection means in said air inlet passage for concentrating the air flow towards said first exit slot along said boundary wall of the chamber.

2. A meter according to claim 1 wherein the air inlet passage has a cross-sectional area transverse to said displacement of the piston, and the deflection means comprises a wall member occupying not substantially less than 50% of said cross-sectional area in a region of the air inlet passage further from said first side region than said second side region of the chamber.

3. A meter for measuring the ventilatory capacity of a subject, comprising: a hollow body, the hollow of said body providing a chamber; an air inlet passage to the chamber; a piston having an end position within the chamber adjacent said air inlet passage; resilient biasing means urging the piston towards said end position in the chamber, the piston being displaceable from said end position by the subject blowing through the inlet air passage into the chamber; side walls of said hollow body defining first and second laterally opposite side regions of the chamber extending away from said inner inlet passage; an air exit slot extending along said first side region of the chamber away from said air inlet passage for the escape of air from the chamber to be increasingly opened by said displacement of the piston from its end position; indicator means for indicating the maximum said displacement of the piston; and deflection means in said air inlet passage offset laterally away from said first side region for concentrating the air flow towards said first side region.

4. A meter according to claim 3, wherein the chamber air inlet passage has an entry generally in the form of an annulus and said wall member blocks a sector of said annulus extending not substantially less than 180° around said annulus.

5. A meter according to claim 4 wherein the chamber inlet comprises a central boss and an outer periphery surrounding said boss, a convex face of said boss being presented to the incoming air flow and said boss and said outer periphery forming said annulus.

6. A meter for measuring the ventilatory capacity of a subject, comprising: a hollow body, the hollow of said body providing a chamber; an air inlet passage to said chamber; a tubular mouthpiece connected to said hollow body for directing air flow to said inlet passage, said mouthpiece having a longitudinal axis extending in the direction of said air flow; a piston having an end position within the chamber adjacent said air inlet passage; resilient biasing means urging the piston towards said end position in the chamber, the piston being displaceable from said end position by the subject blowing through the mouthpiece and through the air inlet passage into the chamber; side walls of said hollow body defining first and second laterally opposite side regions of the chamber extending away from said inner inlet passage; an air exit slot extending along said first side region of the chamber away from said air inlet passage for the escape of air from the chamber, said exit slot being increasingly opened by said displacement of the piston from its end position; indicator means for indicating the maximum said displacement of the piston; and deflection means in said air inlet passage for concentrating the air flow towards said first side region of the chamber, said deflection means comprising a boundary wall inclined with respect to the mouthpiece longitudinal axis in said direction of air flow and toward said first side region of the chamber.

7. A meter according to claim 6, wherein the boundary wall has respective ends that are leading and trailing in said air flow direction and said inclination of the boundary wall reduces towards its trailing end.

8. A meter for measuring the ventilatory capacity of a subject, comprising: a hollow body, the hollow of said body providing a chamber; an air inlet passage to the chamber; a piston having an end position within the chamber adjacent said air inlet passage; resilient biasing means urging the piston towards said end position in the chamber, the piston being displaceable from said end position by the subject blowing through the inlet air passage into the chamber; side walls of said hollow body defining first and second laterally opposite side regions of the chamber extending away from said inner inlet passage; an air exit slot extending along said first side region of the chamber away from said air inlet passage for the escape of air from the chamber to be increasingly opened by said displacement of the piston from its end position; indicator means for indicating the maximum said displacement of the piston; deflection means in said air inlet passage for concentrating the air flow towards said first side region of the chamber; and flow smoothing means in the path of the air flow past the deflection means.

9. A meter according to claim 8, wherein said flow smoothing means comprises a series of spaced vanes.

10. A peak flow meter comprising: a body forming a generally cylindrical chamber; an air inlet passage to one end of the chamber; an air exit slot along a side wall of said chamber and extending away from said one end of the chamber; a piston in the chamber having a position of rest adjacent said one end of the chamber; resilient biasing means urging the piston towards said rest position, the piston being displaceable from said rest position by a subject blowing through said air inlet passage into the chamber, said air exit slot being increasingly opened to the air blown into the chamber by said displacement of the piston against the resilient biasing means; indicator means on the body for indicating the maximum said displacement of the piston; and a wall member in said air inlet passage forming deflection means which incline toward said air exit slot for concentrating the air blown into the chamber towards that side wall in which the exit slot is situated.

11. A meter for measuring the ventilatory capacity of a subject, comprising a chamber, an air inlet passage to chamber, a piston having an end position within the chamber adjacent said air inlet passage, resilient biasing means urging the piston towards said end position in the chamber, the piston being displaceable from said end position by the subject blowing through the inlet air passage into the chamber, an air exit slot for the escape of air from the chamber extending along a side of the chamber away from the air inlet passage to be increasingly opened by said displacement of the piston from its end position, indicator means for indicating the maximum said displacement of the piston, the air inlet passage having an entry generally in the form of an annulus deflection means in said air inlet passage comprising a wall member situated in a laterally offset position in said annulus, away from the side of the chamber in which the exit slot is situated, and concentrating the air flow towards said side of the chamber in which the exit slot is situated, said wall member blocking a sector of said annulus extending not substantially less than 180° around said annulus.

12. A meter for measuring the ventilatory capacity of a subject, comprising a chamber, an air inlet passage to the chamber comprising a tubular mouthpiece having a longitudinal axis extending in the direction of airflow through said mouthpiece, a piston having an end position within the chamber adjacent said air inlet passage, resilient biasing means urging the piston towards said end position in the chamber, the piston being displaceable from said end position by the subject blowing through the inlet air passage into the chamber, an air exit slot for the escape of air from the chamber extending along a side of the chamber away from the air inlet passage to be increasingly opened by said displacement of the piston from its end position, indicator means for indicating the maximum said displacement of the piston, and deflection means in said air passage at the inlet to the chamber for concentrating the air flow towards said side of the chamber in which the exit slot is situated, said deflection means comprising a boundary wall that is inclined with respect to the mouthpiece longitudinal axis such that said boundary wall slopes towards the slot in the chamber side, the boundary wall having respective ends that are leading and trailing in said air flow direction and said slope of the boundary wall reduces towards its trailing end.

13. A meter for measuring the ventilatory capacity of a subject, comprising a chamber a boundary wall, an air inlet passage to the chamber, a piston having an end position within the chamber adjacent said air inlet passage, resilient biasing means urging the piston towards said end position in the chamber, the piston being displaceable from said end position by the subject blowing through the inlet air passage into the chamber, an air exit slot for the escape of air from the chamber said air exit slot extending along said boundary wall, away from said air inlet passage, to be increasingly opened by said displacement of the piston from its end position, indicator means for indicating the maximum said displacement of the piston, deflection means in said air inlet passage at the inlet to the chamber for concentrating the air flow towards said boundary wall of the chamber in which the exit slot is situated, and smoothing means adjacent the deflection means for the air flow passing said deflection means into the chamber.

* * * * *